United States Patent [19]
Xu

[11] Patent Number: 5,912,735
[45] Date of Patent: Jun. 15, 1999

[54] LASER/WHITE LIGHT VIEWING LASER IMAGING SYSTEM

[75] Inventor: James Jianguo Xu, Sunnyvale, Calif.

[73] Assignee: KLA-Tencor Corporation, San Jose, Calif.

[21] Appl. No.: 08/902,370

[22] Filed: Jul. 29, 1997

[51] Int. Cl.$^6$ ........................................................ G01B 9/02
[52] U.S. Cl. ............................................ 356/345; 359/577
[58] Field of Search .................................... 356/345, 359, 356/360, 369; 359/629, 630, 638, 639, 640, 577, 583, 834, 837

[56] References Cited

U.S. PATENT DOCUMENTS

5,479,252   12/1995   Worster et al. ........................... 356/237

*Primary Examiner*—Frank G. Font
*Assistant Examiner*—Tu T. Nguyen
*Attorney, Agent, or Firm*—Skjerven, Morrill, MacPherson, Franklin & Friel, LLP; Alan H. MacPherson; Daniel P. Stewart

[57] ABSTRACT

A laser imaging system having contemporaneous laser/white light viewing such that substantially only the wavelength of the spectral line of the laser light of the confocal portion of the laser imaging system is blocked by a holographic notch filter positioned in front of the white light image capture device (e.g., a video or CCD camera) to provide a white light image characterized by the natural white light image having been preserved and whereby substantially all of the reflected white light spectrum is transmitted by the holographic notch filter. In a second aspect of the invention, a novel bright field cube includes a beam splitter dimensioned to effectively eliminate the contrast bands typical of laser confocal images of the prior art resulting from interference fringes in the beam splitter to provide enhanced image detail of specimen structures.

10 Claims, 4 Drawing Sheets

LASER/WHITE LIGHT VIEWING LASER IMAGING SYSTEM

CROSS-REFERENCE TO RELATED APPLICATIONS

This application is related to the commonly owned U.S. Pat. No. 5,479,252, entitled "Laser Imaging System For Inspection and Analysis of Sub-Micron Particles," by Worster et al., issued Dec. 26, 1995, the disclosure of which is hereby incorporated by reference.

BACKGROUND OF THE INVENTION

1. Field of the Invention

This invention relates to laser imaging systems and, in particular, to a laser imaging system permitting viewing under simultaneous laser and white light illumination for use in analyzing defects on semiconductor wafers.

2. Related Art

Semiconductor chip manufacturers have increasingly sought to improve yields in their production processes. Key to this effort is the reduction of particulate contamination during wafer processing. As the line widths of features on the chip have shrunk from 1.0 microns several years ago to 0.35 micron and below today (with line widths approaching 0.18 micron or less expected in the next few years), the ability to detect and control smaller and smaller particles to achieve higher degrees of cleanliness has become paramount. Additionally, production of acceptable chips requires accurate performance of each of the process steps carried out on the wafer. The value of product on each wafer has also increased dramatically, due to the increasing complexity of semiconductor devices (many more layers and process steps) and the development of larger wafers (up to 300 mm diameter), further accentuating the need for defect detection and control.

Instrument suppliers have addressed a portion of this problem by developing defect detecting systems which scan wafers (wafer scanners) during production for anomalous optical sites that are characteristic of particulate contamination (but may represent other flaws as well). An review of currently commercially available defect analysis devices is presented in commonly owned U.S. Pat. No. 5,479,252, entitled "Laser Imaging System For Inspection and Analysis of Sub-Micron Particles," by Worster et al., issued Dec. 26, 1995, the disclosure of which has incorporated by reference.

Laser imaging systems for sub-micron particle structure evaluation provide advantages over other types of defect analysis devices including allowing hands-off operation under class 1 cleanroom conditions, and "revisiting" defects on production semiconductor wafers, where the defects are first detected (but not analyzed or evaluated) by conventional wafer scanners.

As noted above, the decreasing line widths of features on current and future semiconductor chips increase the importance of detection of contaminants and other defects having a diameter, width, or other characteristic dimension on the order of 0.1 to 0.3 microns. The visible light, off-the-shelf microscopes currently being used in defect review stations lack sufficient resolution to resolve defects of such small size, or to resolve this size structure on larger defects to aid in identification. Visible light scanning microscopes (both white light and laser-based) that are built by modifying off-the-shelf microscopes can improve the resolution significantly, but they are currently in limited use, mostly as part of complex and expensive research setups. Additionally, the use of conventional microscopes increases the risk of contamination of the semiconductor chips during the review process, since a (relatively dirty) human is in close proximity to the wafer surface and because the presence of the microscope causes turbulent flow near the wafer which tends to pull in nearby contaminants to the wafer.

Unlike other devices used for semiconductor defect analysis, a laser imaging system will not damage samples or slow processing, and costs significantly less to implement than, for example, a scanning electron microscope (SEM). Moreover, while SEMs can produce images with resolution on the nanometer scale, they have certain limitations. For example, the SEM image has an extended depth of field, like a photograph taken through a high f-stop aperture, but this image contains no quantitative depth information. Some methods of dealing with this deficiency are sample tilting or coating to produce a "shadowing" effect or perspective change, but these methods require additional process steps and cost, may damage the wafer, and do not completely resolve the problem.

Laser imaging systems are capable of operating in cleanrooms having a class 1 cleanroom requirement. Laser imaging system are capable of producing a three dimensional image, using simple image rendering techniques, which provides quantitative dimensional information. The image can be stored and recalled for later viewing. The image can be rotated or tilted or shaded, with correct perspective maintained, without necessity for sample tilting or coating. Additionally, the laser imaging system has the ability to perform sub-surface viewing of defects lying beneath dielectric layers, an ability unavailable to the SEM. Combined with three-dimensional analysis software, a user is able to examine cross sections of the defect and surrounding material, and to assess the impact on circuit layers of the wafer. Since laser imaging systems are capable of resolutions on the order of 0.1 to 0.2 microns, they may be used for metrology as well.

A laser imaging system typically utilizes confocal laser scanning microscopy techniques, including multi-line visible light lasers, and can be optionally fitted with an ultraviolet laser, improving resolution even further due to the shorter wavelengths of the ultraviolet light. White light imaging, in addition to laser imaging is featured in laser imaging system. White light imaging permits conventional microscope images to be attained, and by use of a video camera or charge coupled device (CCD), the image may be displayed on a video monitor or computer display without undesirable proximity of the operator to the wafer.

The white light microscope image may be produced either alone or simultaneously with the live laser image. Simultaneous viewing under both white light and laser light is desirable in that the white light image provides color information of the defect and facilitates locating and identifying the defect, while the laser confocal image provides three-dimensional information of the defect.

To enable simultaneous viewing under both white light and laser light, a color filter is positioned between the illuminated portion of the wafer and the CCD camera to block the laser light from entering the camera. For example, where an argon ion laser is used to illuminated the wafer, a color filter blocking any wavelengths below 550 nm will effectively block off the laser lines between 458–515 nm. The purpose of the filter is to prevent the reflected laser light from over-saturating the image at the video camera, thus permitting the camera to acquire the white light image without being "blinded" by the laser.

The approach of currently available laser imaging systems, however, suffer serious limitations in their ability to provide simultaneous viewing of a semiconductor wafer under both white light and laser light. For example, the color filter typically used to filter out the laser light from the CCD camera removes a significant portion of the white light spectrum resulting in an unnaturally hued white light image. For example, where a 550 nm cut-off filter is used to remove wavelengths associated with an argon ion laser, the white light picture is rendered yellow, thus obscuring some colored defects. Moreover, in laser imaging systems having simultaneous viewing capability, the autofocus feature is typically performed with the color filter in place. Accordingly, if a user wishes to visit defects in white light only, the color filter must be switched in and then out of the optical path, thus significantly increasing the process time required to investigate a defect.

A further limitation of laser imaging systems having simultaneous white light/laser light viewing capability are the laser light interference fringes caused by the bright field cube of the microscope optics. The effect of these interference fringes is to produce bands of increased contrast in the laser image. These bands tend to obscure details of the observed structures on the semiconductor wafer, thus compromising the resolution of the confocal laser image.

Accordingly, there is a need for a laser imaging system capable of simultaneously producing white light and laser confocal images without compromising the color integrity of the white light image, and without producing a laser confocal image having contrast bands associated with interference fringes produced in an optical element of the laser imaging system. There is also a need for a laser imaging system capable of simultaneous imaging under both white light and laser light that permits a white light imaging mode only without having to remove and then re-insert the color filter during autofocus.

SUMMARY OF THE INVENTION

According to the invention, a laser imaging system that permits true simultaneous laser/white light imaging, has several distinct advantages over conventional laser imaging systems for sub-micron particle structure evaluation. In one embodiment, the laser imaging system comprises a conventional white light microscope and a laser confocal microscope. The white light microscope portion of the laser imaging system of this invention uses a white light source, the light from which is transported via a vertical illuminator, a bright field (BF) cube, and an objective to the sample under investigation. The return light from the sample passes through the same objective, BF cube, and into a CCD or video camera whereby a white light image is produced. The laser confocal microscope of the laser imaging system of this invention includes a laser light source, and a wavelength selection filter for selecting a predetermined wavelength of laser light with which to illuminate the sample. The predetermined wavelength of laser light passes through the laser confocal optics, through the BF cube, an objective, and is focused on the sample. The return laser light from the sample retraces the incoming laser light all the way up to the confocal optics where it is directed to a detection subsystem instead of going back to the laser light source.

In accordance with one aspect of the laser imaging system of this invention, the broad-spectrum, wavelength selection filter positioned at the output of the laser is replaced with a narrow spectral line bandpass filter that permits substantially only one wavelength of light to pass from the laser, and the broad-spectrum color filter positioned before the CCD or video camera is replaced with a holographic notch filter that blocks substantially only the spectral line having the wavelength of the filtered laser light. While the holographic notch filter in front of the CCD blocks the laser light, it transmits substantially all of the remainder of the visible spectrum to provide a true white light viewing capability. The notch is so narrow that the filter cuts out only a tiny fraction of the whole white light spectrum. As a result, and unlike the high or low pass cut-off color filters of the prior art, the natural appearance of the white light image produced by the laser imaging system of this invention is preserved, and is characterized by an improved color balance, even with the notch filter in place. Since the notch filter does not change the color of the white light, it can remain in the optical path at all times regardless of which viewing mode a user chooses including a white light imaging only mode. This feature permits true white light imaging without having to remove the color filter, as is done in laser image systems of the prior art, resulting in an increase in throughput for white-light only viewing.

The wavelength selection filter positioned at the output of the laser light source is selected based on the wavelength to be passed (the transmitted spectral line) as well as the wavelengths of adjacent spectral lines to be suppressed (adsorbed spectral lines). The transmitted wavelength of the spectral line will be dependent upon the particular laser imaging task to be accomplished. It is important to provide a selection of wavelengths of laser light to perform imaging to overcome absorption, reflection, and interference problems that can occur for a specific wavelength for a given material. That is, one wavelength will not give good results for all materials, film thicknesses, and surface properties. Additionally, in many cases, it is desirable to observe through one or more top layers of material (typically dielectric) which will reflect or absorb some wavelengths strongly, but will allow transmission of others to perform the imaging desired. Various lasers including but not limited to argon, helium-neon, helium cadmium, and continuous dye lasers may be used to supply light at the appropriate wavelength.

It is understood by those practicing in the art that the selection of the holographic notch filter will complement the selection of the spectral line bandpass filter. In other words, the holographic notch filter positioned in front of the white light CCD camera will necessarily block substantially only that wavelength of transmitted laser light from the spectral line bandpass filter. Should the user replace the spectral line bandpass filter to permit selecting a transmitting a different spectral line than that transmitted by the previous bandpass filter, the holographic notch filter must also be modified to block substantially only the wavelength of the newly selected spectral line. By narrowing the bandpass of the wavelength selection filter to a single spectral line, and by similarly narrowing the width of the of the CCD color adsorption filter to the same spectral line, the laser imaging system of this invention is able to provide true white light imaging of a specimen, even with the CCD notch filter positioned in the white light optical path, and even with the laser light source turned on.

I have discovered that the contrast bands in the displayed confocal laser image of the prior art are associated with laser light interference fringes originating in the BF cube. By way of theory and explanation, and not by way of limitation, I have determined that these interference fringes are caused by interference between direct going laser light rays and laser light rays that have been reflected in the beam splitter of the BF cube; i.e., they are equal-inclination interference fringes.

In accordance with a second aspect of the laser imaging system of this invention, I have also discovered that by selecting an appropriate beam splitter thickness, the fringe spacing can be made smaller than the fill width at half-maximum of the fringe peak. As the fringe interval becomes smaller the interference peaks appear to blend together causing the contrast bands from the interference fringes to seemingly disappear from the displayed laser image. The modified BF cube of this invention includes a beam splitter inside the cube having a predetermined thickness. No noticeable degradation of the white light image quality occurs when using the modified BF cube of this invention.

The laser imaging system of this invention provides a true white light image under simultaneous laser/white light illumination of the subject specimen. The combination of the spectral line bandpass filter and the complementary notch filter provide a white light image under simultaneous illumination that is substantially equivalent to a white light only mode with the notch filter removed from the white light optical path. Accordingly, white light imaging may be performed with the notch filter left in place in the white light optical path, thus increasing the throughput when in a white light only imaging mode.

Additionally, the laser imaging system of this invention provides a laser confocal image that is free of the contrast bands associated with the interference fringes caused by the BF cube and that is typical of the confocal images of the prior art. The resultant confocal image provides improved detail of the specimen structure as the contrast bands, which make observing the detailed structure more difficult, are in effect eliminated.

BRIEF DESCRIPTION OF THE DRAWINGS

Further advantages and embodiments of the present invention will become apparent when the following detailed description is read in conjunction with the attached drawings, in which.

DETAILED DESCRIPTION OF EMBODIMENTS
OF THE INVENTION

A laser imaging system according to the invention provides contemporaneous, or substantially simultaneous, laser/white light viewing and is used to analyze defects on semiconductor wafers, or other objects having surface defects, that have optionally been previously detected by patterned wafer defect detecting systems (wafer scanners) or the like. Other applications are possible, for example, defect analysis of magnetic and optical disk surfaces. The laser imaging system replaces optical microscope review stations now utilized in the semiconductor fabrication environment to examine detected optical anomalies that may represent wafer defects. In addition to analyzing defects, the laser imaging system can perform a variety of microscopic inspection functions including defect detection and metrology.

Figure 1:
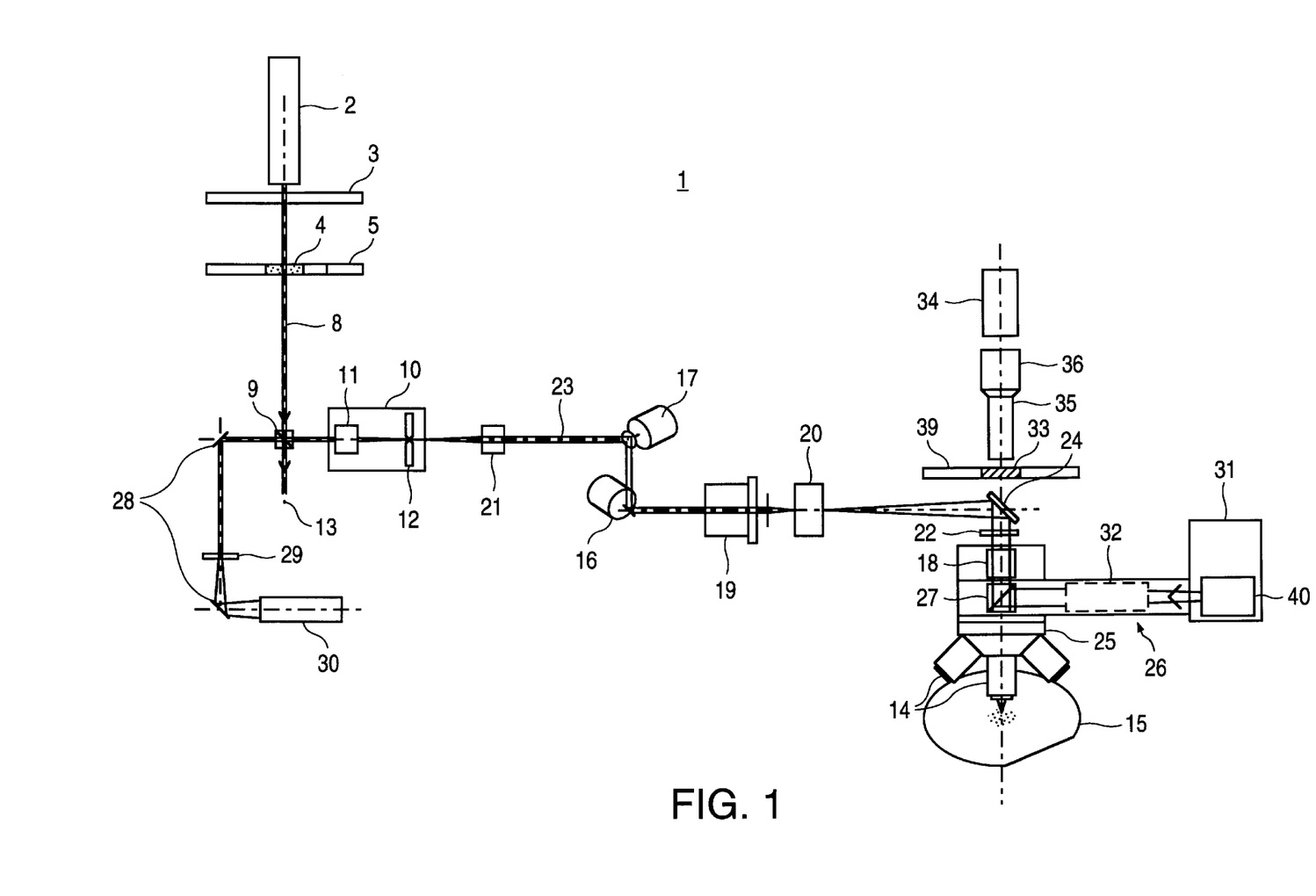
FIG. 1 is a schematic diagram of a laser imaging system according to the invention illustrating the operation of the laser imaging system.

FIG. 1 is a schematic diagram of one embodiment of the laser scanning microscope optics (the "optics head") 1 of a laser imaging system according to the invention and illustrates the operation of the optical portion of a laser imaging system. The optics head includes a laser, confocal beam-scanning optics, and ultraviolet and visible spectrum photo detection electronics, together with commercial microscope components to achieve high quality real time confocal images. A laser imaging system utilizing the optics head will produce a complete XY-scanned laser image, in a single plane of focus, at video rates. The resulting image is displayed on a high resolution monitor, also in real time. Thus, the operator can scan through different levels of focus in real time, as with a conventional microscope.

The optics head 1 of the laser imaging system of this invention uses the basic principles of confocal microscopy, in which illuminating light passes through a pinhole, and the image of this pinhole is then cast by the system optics on the sample to be viewed. The light scattering from the sample returns through the system optics to the pinhole, but only light from the focal plane of the imaging (objective) lens returns through the pinhole, i.e., light from the plane through the sample at which it is desired to obtain imaging data.

Optics head 1 includes an air cooled, multi-line argon ion laser 2 which provides up to six different wavelengths of light for imaging surfaces and structures in semiconductors. An example of a laser that can be used with the invention is the Model 2204-25ML air-cooled argon ion laser produced by Uniphase Corporation, San Jose, Calif. As previously mentioned, it is important to be able to preselect the spectral line from a selection of wavelengths of laser light to perform the confocal imaging so that absorption, reflection, and interference problems that can occur for a specific wavelength for a given material may be mitigated by the selection of an alternate spectral line.

Figure 2:
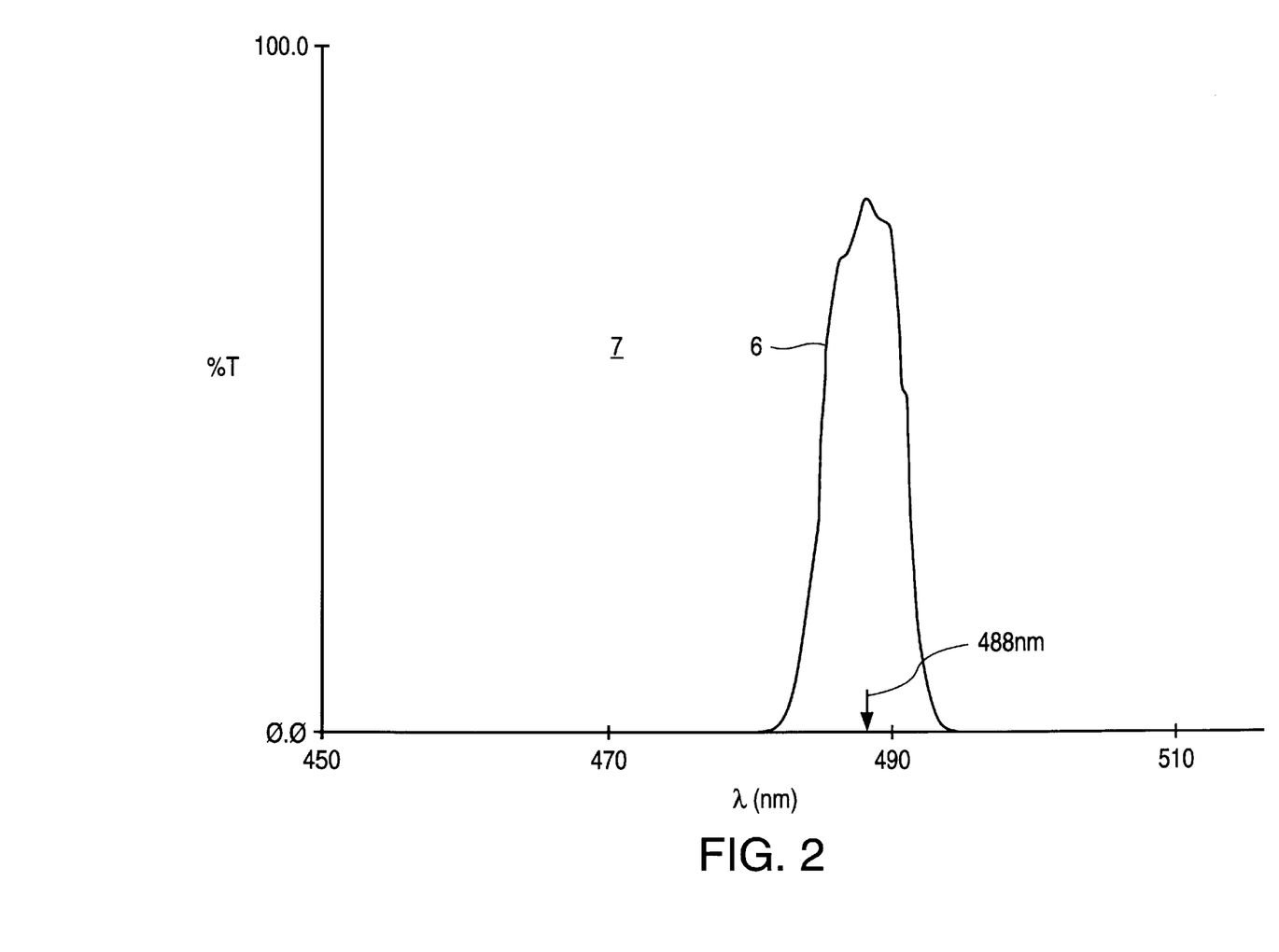
FIG. 2 is a transmission spectra of a spectral line bandpass filter suitable for transmitting laser light at 488 nm.

Argon laser 2 produces polarized light at several discrete wavelengths. The light passes through an optional light intensity attenuator 3, followed by spectral line bandpass filter (or wavelength selection filter) 4 mounted on a conventional computer controlled filter wheel 5 within optics housing section (not shown). The spectral line bandpass filter 4 is selected to pass substantially only a single spectral line from the argon laser. A spectral line bandpass filter suitable for transmitting substantially only the 488 nm spectral line from argon laser 2 is available from Omega Optical of Brattleboro, Vt., as part no. 487RDF7.4. FIG. 2 shows the transmission spectra 6 of the 488 nm Omega Optical filter. The transmission peak 7 is very sharp and passes light having a wavelength of between about 483 nm and 490 nm. In particular, the 488 nm spectral line of the argon laser is passed while other spectral lines are attenuated. Other spectral line bandpass filters are available from the same source for other wavelengths.

Referring once again to FIG. 1, the light from the transmitted spectral line 8 having the selected wavelength passes from the bandpass filter 4 to polarizing beam splitter 9. Polarizing beam splitter 9 is attached to spectral line bandpass filter 4 using conventional optical mounts. Polarizing beam splitter 9 preferentially reflects light only of the proper polarization and directs the light to spatial filter 10. The spatial filter comprises focusing optics 11 and a pinhole aperture 12. The polarization of the light emitted from laser 2 is oriented so that most of the light is reflected by polarizing beam splitter 9 at ninety degrees into the focusing optics 11 of spatial filter 10. A small portion 13 of the laser light passes through polarizing beam splitter 9 to a beam dump (not shown) mounted behind polarizing beam splitter 9, where the light is absorbed. A polarizing beam splitter for use with the invention is available from Melles Griot of Irvine, Calif. as part no. 03PBB003.

Spatial filter 10 consists of focusing optics 11 which expands the beam and then focuses it on a pinhole aperture 12. The diameter of the pinhole aperture 12 is selected according to well-known known techniques to re-image the light through downstream optics and a selected one of a plurality of objective lenses 14 to produce a diffraction-limited spot on wafer 15. The diameter of the pinhole aperture 12 is also selected to allow easy alignment of the beam of light and a significant amount of high power light to pass through the aperture. A spatial filter for use with the invention is available from Melles Griot of Irvine, Calif. as Compact Spatial Filter Newport/910. Spatial filter 10 is attached to polarizing beam splitter 9 by conventional optic mounts.

Subsequent optics include collimator lens 21. The collimator lens 21 collimates the laser light after it has exited the pinhole aperture. The collimated light 23 is directed to mirrors mounted on X-direction line scanner 16, and Y-direction page scanner 17. An X-Y beam scanner 16 and 17 for use with the invention is available from General Scanning of Watertown, Mass. as part no. 000-3011003. X-Y beam scanners 16 and 17 are attached to spatial filter 10 by conventional optics mounts. The mirrors in X and Y beam scanners 16 and 17 can oscillate their angle with respect to the beam of light passing through the scanners. Each of X and Y beam scanners 16 and 17 includes an oscillating galvanometer, one galvonometer being a high speed resonant unit operating at 8 kHz to accommodate the high-speed X direction line scanning, and the other galvanometer being a servo controlled unit, operating at 13 or 26 Hz (but capable of other speeds) to perform the frame, or page, scanning in the Y-direction. The servo steps in small increments, so that the X and Y beam scanners 16 and 17 trace out a raster pattern in space. A raster scan of 256 or 512 lines is produced at approximately 26 or 13 frames per second, and is imaged at the back focal plane of the tube lens 18.

This raster pattern is imaged in space by the scan lens 19 in the plane of the field lens 20. A scan lens 19 for use with the invention is available from Applied Optics of Pleasanton, Calif. as part no. 000424. Scan lens At is attached to X-Y beam scanners 16 and 17 by conventional optical mounts. The field lens 20 serves to collect high angle light, providing a more uniform brightness across the raster pattern and allowing more light to reach the tube lens 18, described below, without distorting the image. The tube lens 18 and objective lenses 14, described in more detail below, are standard infinity corrected optics.

Laser/white light beam splitter 24 directs the laser light through quarter wave plate 22 and through tube lens 18. Quarter wave plate 22 is positioned to convert the linearly polarized laser light to circularly polarized laser light. A quarter wave plate for use with the invention is available from Melles Griot of Irvine, Calif. as part no. 02WRM005. The tube lens 18 is typically attached to beam splitter 24 by a conventional optical mount and works with objective lens 14 to de-magnify the raster scanned pinhole image and project it on the wafer 15. A tube lens 18 for use with the invention is available from Olympus of Japan as part of their vertical illuminator model 5LM220.

The laser light proceeds through bright field cube 27. The bright field (BF) cube 27 of this invention has been improved to eliminate the laser light interference patterns set up in the beam splitter portion of the BF cube. I have discovered that by selecting an appropriate beam splitter thickness, the fringes can be effectively eliminated. In other words, since the fringe interval is inversely proportional to the beamsplitter depth in the BF cube, by increasing the beam splitter depth, the fringe interval is reduced, to the point where the interference fringe peaks appear to "blend" together giving the appearance that the fringes have disappeared. The following Table I shows the empirical results obtained with BF cubes having beamsplitters of varying depth.

TABLE I

| SAMPLE No. | BEAMSPLITTER DEPTH (MM) | OBSERVED FRINGE INTERVAL ($\mu$) |
|---|---|---|
| 1 | 1 | 1.65 |
| 2 | 2.5 | 0.6 |
| 3 | 6.5 | No Fringe Visible |

Figure 3:
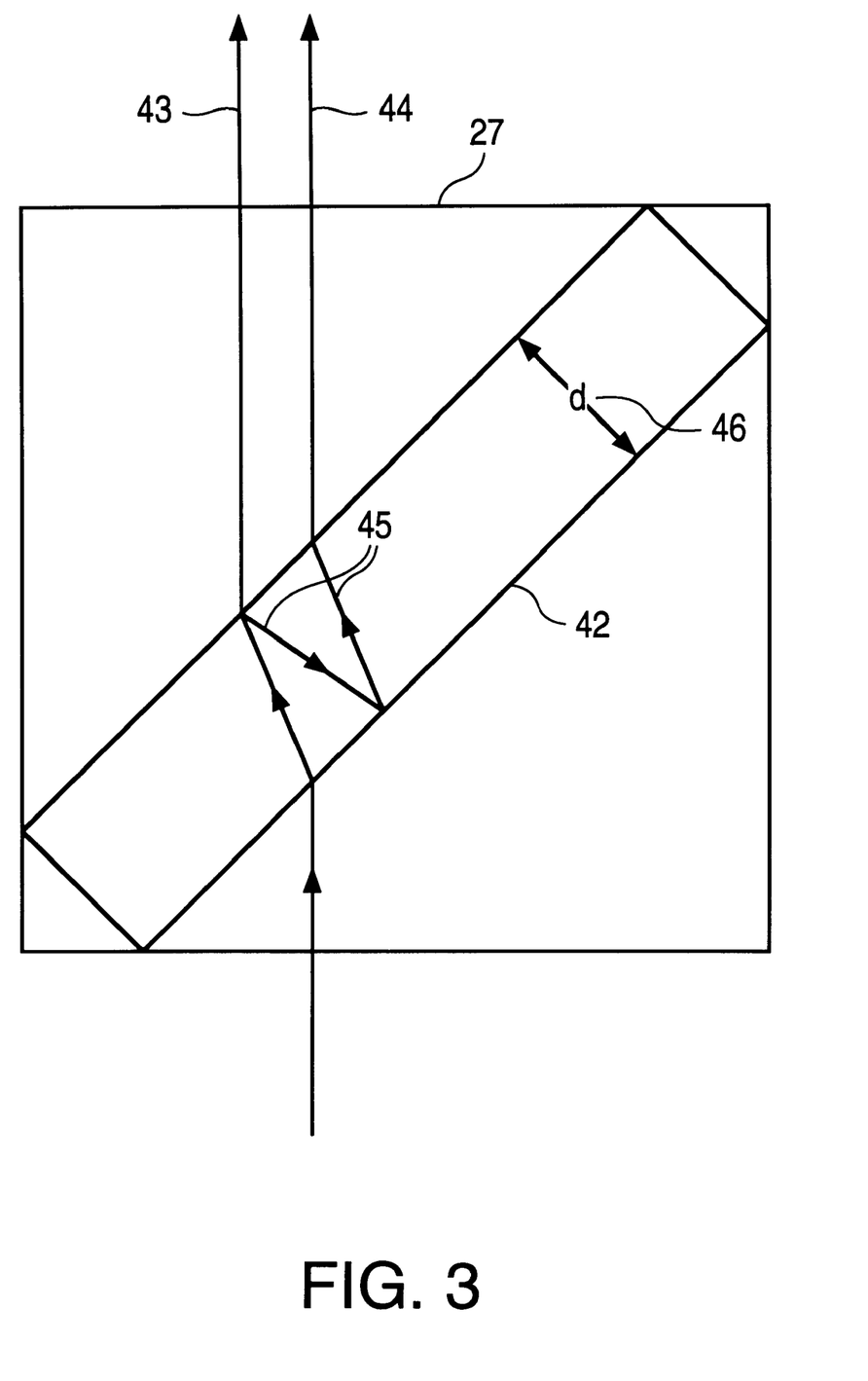
FIG. 3 is a cross-section diagram of the bright field cube of this invention.

As the beamsplitter depth approaches 6.5 mm, the fringe interval becomes small, to the point that the fringes seemingly disappear. At a beamsplitter thickness of 6.5 mm, the fringe interval is approximately equal to 0.25 microns and is already smaller than the full width at half-maximum of the fringe peak. As a result, the fringes are seemingly no longer visible, thus eliminating the contrast bands, typical of confocal laser images of the prior art. FIG. 3 shows a BF cube 27 having a beamsplitter 42 therein. Interference fringes are formed when a first ray 43 of outgoing laser light interferes with a second ray 44 of outgoing laser light that has undergone internal reflection 45 within the beamsplitter portion 42 of the BF cube 27. I have discovered that if the beam splitter is manufactured with a sufficient depth 32, then the fringe interval may be reduced such that the fringes seemingly disappear. As a BF cube having a beamsplitter with a depth of 6.5 mm is a novel feature of this invention, a commercial source has not been presently identified. It is understood that a person skilled in optics should be able to either make the modified BF cube as disclosed herein, or else have one custom made.

After having passed through the BF cube, the laser light spot is focused by the objective lens 14 in the focal plane of the objective lens 14. Objective lenses 14 suitable for use with the invention are available from Olympus of Japan by specifying 100×BF 1-LM590. Many interchangeable lenses are available. Objective lenses 14 are mounted on a computer controlled motorized turret 25 that enables automatic changing of objective lenses 14 and autofocus (one lens is focused and focus offsets stored in the computer are used to automatically focus the other lenses) of each objective lens 14. A turret for use with the invention is available from Olympus of Japan as part no. BL0920. Turret 25 is designed to accommodate three to six objective lenses 14, and can handle low power (magnifications of 5, 10 and 20 times actual size) as well as medium power (magnification of 50 times actual size) and high power, high N.A. (numerical aperture, a conventional designation for the light gathering property of an objective lens in which higher numbers indicate a broader cone of gathered light) objective lenses 14 (magnifications of 100 and 150 times actual size and 0.95 N.A.). Turret 25 is attached to tube lens 18, described in more detail below. Turret 25 and a vertical illuminator 26 containing tube lens 18 as a standard component are mounted together with a flange and held by a locking screw. The turret/illuminator assembly bolts to the optics baseplate.

According to the principles of confocal imaging, the laser light striking wafer 15 is scattered and a portion of the light reflected back into objective lens 14, returning through the optical path described above. The light continues back along the path through the field lens, scan lens 19, and mirrors of X-Y scanner 16 and 17. As the returning light passes through quarter wave plate 12, the returning light is converted to light linearly polarized and 90° out of phase with respect to the polarization of the light originally emitted by laser 2. The returning laser light continues back up the optical path until the light reaches the pinhole aperture 22 of spatial filter 10. If the light spot was in focus on the sample, the image is imposed on the aperture. If the light spot was out of focus on the sample, very little light returns through the aperture. Consequently, signals in the confocal optics get darker, not merely blurred, as occurs with conventional optics, when the sample is out of focus. Light which passes through the aperture reaches the polarizing beam splitter 9, which, being oppositely polarized, passes through polarizing beam splitter 9 undeviated, is reflected by folding mirrors 28, is passed through photo detector diverging lens 29, and is imaged on the photodetector 30.

By measuring the light intensity at each XY location of the raster scan, a map of light intensity in the focal plane of the objective lens 14 is constructed. This map can either be stored in the memory of the system control computer (not shown), or analyzed by surface data processor (not shown), which stores the readings, and makes a comparison of the intensity with previously stored maps from other scans, as described below. The light intensity map is also written directly into the video memory of the system control computer and may be displayed live on the computer display (not shown) in an appropriate window.

To obtain a three dimensional image, the optics head works with the fine z-stage control (not shown) to develop an expanded depth-of-field image. The sample height is stepped over a pre-selected vertical interval (typically 12 nm or some multiple thereof) using the fine z-stage control. After each complete raster scan at a particular sample height, the height of the sample is changed using the fine z-stage control, and a new raster scan performed, as described above, to obtain a map of light intensity in the focal plane of objective lens 14 (at the new sample height) by measuring the light intensity at each XY location of the raster scan.

An X-Y stage control (not shown) is used to position the defect or region of interest in the field of view. The X-Y stage control is then held still while the fine z-stage control is used as described above.

The capability for white light imaging, in addition to the laser imaging described above, is another feature of laser imaging systems. With continued reference to FIG. 1, white light is generated in the white light lamphouse 31, is directed through the vertical illuminator optics 32 positioned within the vertical illuminator 26, and through the BF cube beam splitter 27 whereby the white light is directed through the microscope objective 14 and onto the semiconductor wafer 15. The reflected white light travels back through the BF cube beamsplitter 27, through the tube lens 18, and through the laser/white light beamsplitter 24. With the exception of the wavelength of the spectral line of the laser light, substantially the entire spectrum of the white light is transmitted through holographic notch filter 33.

The holographic notch filter transmits substantially all wavelengths except the wavelength of the laser spectral line used to form the confocal laser image. As such, it is selected to complement the spectral line bandpass filter positioned in front of the laser 2. Since substantially the entire visible spectrum is transmitted by holographic notch filter 33, a conventional microscope image wherein the natural color is preserved can be obtained, in addition to the laser image, by using a conventional microscope illuminator 26 and video camera 34, or charge coupled device (CCD). Camera 34 is optically connected to the white light image via a video camera coupler comprising a photo-eyepiece 35 and an MTV adapter 36. The white light imaging is accomplished without the use of microscope eyepieces that would result in undesirable proximity of the operator to the wafer being analyzed that may result in contamination of the wafer. Rather, the microscope image is displayed on a computer display (simultaneously with the laser image, if desired), either in a separate window on computer display (not shown), using appropriate software, or on a separate video monitor display (not shown).

The white light microscope image is produced alone or simultaneously with the live laser image by video camera 34 available from Sony, Japan as part no. DXC-950 which views the sample in white light emitted by microscope illuminator 26, and inserted into the optical path by beam splitter 24. A microscope illuminator for use with the invention is available from Olympus of Japan as part no. 5LM220. A beam splitter for use with the invention is available from CVI of Albuquerque, N.M. as part no. BS-488.0-514.5-40-1025-45UNP.

Figure 4:
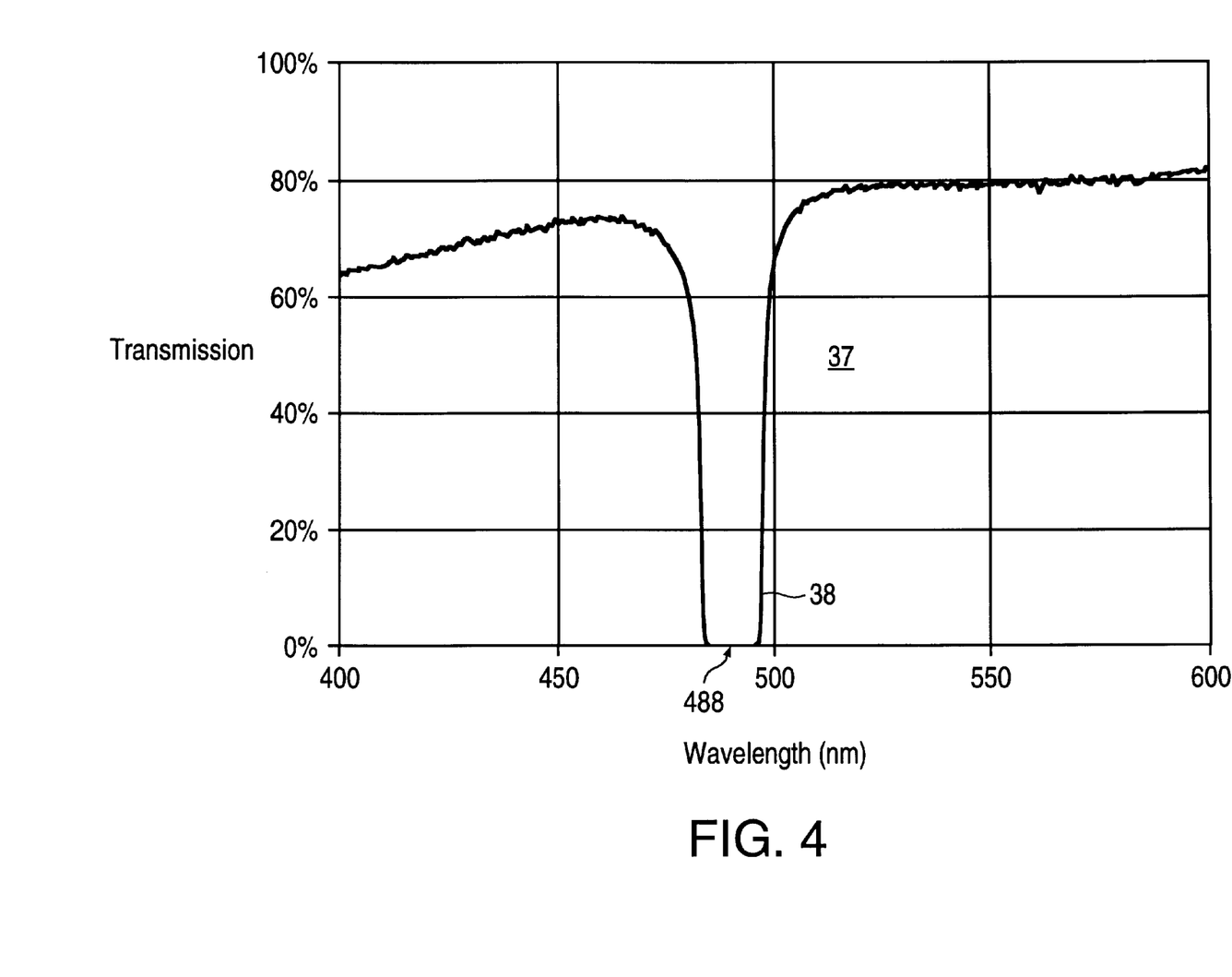
FIG. 4 is a transmission spectra of a holographic notch filter suitable for blocking laser light at 488 nm.

As mentioned above, holographic notch filter 33 blocks the particular laser line in use, but passes broad bands of light having other wavelengths, so that laser light from laser 2 is prevented from saturating the image at video camera 34 with reflected laser light. FIG. 4 shows the transmission spectra 37 of a holographic notch filter that complements the bandpass filter of FIG. 2. As is clearly seen from the spectra, there is absorption peak 38 at approximately 488 nm with rapidly increasing transmission of wavelengths on either side. This holographic notch filter is available from Kaiser Optical of Ann Arbor, Mich. as part no. HNPF-4880-1.0. Video camera 34 and filter wheel 39, upon which is mounted at least one holographic notch filter 33, are mounted on brackets which position video camera 34 and filter 33 in line with beam splitter 24. Beam splitter 24 may be mounted on the turret assembly with conventional optical mounts.

To produce a white light image alone, no elements of the optics head need be removed or modified. Holographic notch filter 33 may stay in place, since the losses associated with filtering out of just a single spectral line are negligible, and substantially all of the visible or ultraviolet spectra (depending on broad spectrum light source 40 in vertical illuminator 26) is transmitted by the filter.

Various embodiments of the invention have been described. The descriptions are intended to be illustrative, not limiting. Thus, it will be apparent to one skilled in the art that certain modifications may be made to the invention as described without departing from the scope of the claims set out below.

I claim:

1. A laser imaging system for imaging a surface of an object, comprising:

a confocal laser imaging system, said confocal laser imaging system includes a laser light source for emitting coherent light having at least one wavelength, and a spectral line bandpass filter positioned at the output of said laser light source for transmitting substantially only a single spectral line from said laser light source for illuminating the object; and a white light imaging system, said white light imaging system includes a broad spectrum light source for illuminating the object, a video camera for receiving a reflected broad spectrum image of the object, and a notch filter positioned in front of said video camera to absorb substantially only the wavelength of said transmitted spectral line from said spectral line bandpass filter, and for transmitting substantially all other visible wavelengths of said broad spectrum light source to permit natural-color white light imaging of the object, wherein said white light imaging system further comprises a bright field cube for permitting bright field white light imaging of the object, said bright field cube includes a beamsplitter therein having a determined thickness sufficient to substantially eliminate viewable contrast lines caused by interference fringes in the bright field cube from the coherent light of said confocal laser imaging system.

2. The laser imaging system of claim 1, wherein the notch filter of the white light imaging system comprises a holographic notch filter.

3. A laser imaging system, comprising:

a) means for producing a confocal laser image of an object, said confocal laser image means includes means for selecting light comprising a single spectral line from a multi-mode coherent light source;

b) means for producing a natural-color white light image of said object, said white light image means includes a white light image recording means and means to absorb substantially only said single spectral line while transmitting substantially all other visible wavelengths reflected from said object, said absorbing means to prevent said single spectral line light from saturating said white light image recording means and to permit substantially simultaneous viewing of both a monochromatic image of said object utilizing said single spectral line and a white light image of said object utilizing wavelengths other than said single spectral line, wherein said white light imaging means further comprises a bright field cube for permitting bright field white light imaging of an object, said bright field cube includes a beamsplitter therein having a predetermined depth sufficient to substantially eliminate viewable contrast lines caused by interference fringes in the bright field cube from said spectral line of said confocal laser image means.

4. The laser imaging system of claim 3, wherein the means to absorb substantially only said single spectral line comprises a holographic notch filter.

5. The laser imaging system of claim 3, wherein the means for producing a natural-color white light image of said object further comprises a broad spectrum light source for illuminating said object.

6. A laser imaging system having a confocal laser imaging system, said confocal laser imaging system includes a laser light source for emitting coherent light having at least one wavelength, and having a white light imaging system, said white light imaging system includes a broad spectrum light source, a video camera for receiving a reflected broad spectrum image, the improvement comprising at least one of:

a spectral line bandpass filter positioned at the output of said laser light source for transmitting substantially only a single spectral line from said laser light source, a notch filter positioned in front of said video camera to absorb substantially only the wavelength of said transmitted spectral line from said spectral line bandpass filter, and a bright field cube for permitting bright field white light imaging of an object, said bright field cube includes a beamsplitter therein having a predetermined depth sufficient to substantially eliminate viewable contrast lines caused by interference fringes in the bright field cube from said coherent light source of said confocal laser imaging system.

7. The laser imaging system of claim 6, wherein the notch filter comprises a holographic notch filter.

8. A bright field cube for permitting bright field white light imaging of an object, said bright field cube includes a beamsplitter therein having a predetermined depth sufficient to substantially eliminate viewable interference fringes set up in said beamsplitter by incident coherent light.

9. A method for substantially contemporaneous laser/white light viewing in a laser imaging system having a confocal laser imaging system, the confocal laser imaging system includes a laser light source for emitting coherent light having at least one wavelength, and having a white light imaging system, the white light imaging system includes a broad spectrum light source for emitting white light, and a video camera for receiving a reflected broad spectrum image, the method comprising the steps of:

a) filtering the laser light source with a spectral line bandpass filter positioned at the output of said laser light source to provide a transmitted laser light having substantially a single spectral line for illuminating the object:

b) filtering the light entering the video camera to absorb substantially only the wavelength of said transmitted spectral line from said spectral line bandpass filter to permit substantially natural-color white light imaging of said object when said object is illuminated by both the coherent light and the white light; and providing a bright field cube for permitting bright filed white light imaging of a specimen, said bright field cube includes a beamsplitter therein having a depth sufficient to substantially eliminate viewable contrast lines caused by interference fringes in the bright field cube from the coherent light of the confocal laser imaging system.

10. The method of claim 9, wherein filtering the light entering the video camera comprises filtering the light entering the video camera with a holographic notch filter.

* * * * *